United States Patent [19]
Baxter et al.

[11] Patent Number: 5,643,253
[45] Date of Patent: Jul. 1, 1997

[54] PHOTOTHERAPY APPARATUS WITH INTEGRAL STOPPER DEVICE

[75] Inventors: Lincoln S. Baxter, Centerville; Norman Farr, Monument Beach; Edward L. Sinofsky, Dennis, all of Mass.

[73] Assignee: Rare Earth Medical, Inc., W. Yarmouth, Mass.

[21] Appl. No.: 468,568

[22] Filed: Jun. 6, 1995

[51] Int. Cl.$^6$ .................................................. A61B 17/36
[52] U.S. Cl. ............................... 606/17; 606/15; 606/7; 606/19
[58] Field of Search ................... 606/14, 15, 16, 606/17, 185, 7, 19; 604/164

[56] References Cited

U.S. PATENT DOCUMENTS

| | | | |
|---|---|---|---|
| Re. 34,544 | 2/1994 | Spears | 604/20 |
| 3,417,745 | 12/1968 | Sheldon | 128/6 |
| 4,233,493 | 11/1980 | Nath | 606/15 |
| 4,336,809 | 6/1982 | Clark | 128/665 |
| 4,585,298 | 4/1986 | Mori | 350/96.1 |
| 4,660,925 | 4/1987 | McCaughan, Jr. | 350/96.15 |
| 4,860,743 | 8/1989 | Abela | 128/303.1 |
| 4,878,492 | 11/1989 | Sinofsky et al. | 123/303.1 |
| 5,053,033 | 10/1991 | Clarke | 606/3 |
| 5,151,096 | 9/1992 | Khoury | 606/15 |
| 5,169,395 | 12/1992 | Narciso, Jr. | 606/7 |
| 5,196,005 | 3/1993 | Doiron et al. | 606/7 |
| 5,207,669 | 5/1993 | Baker et al. | 606/7 |
| 5,209,748 | 5/1993 | Daikuzono | 606/16 |
| 5,219,346 | 6/1993 | Wagnières et al. | 606/16 |
| 5,269,777 | 12/1993 | Doiron et al. | 606/7 |
| 5,281,204 | 1/1994 | Horie et al. | 606/185 |
| 5,337,381 | 8/1994 | Biswas et al. | 385/36 |
| 5,356,382 | 10/1994 | Picha et al. | 606/185 |
| 5,363,458 | 11/1994 | Pan et al. | 385/31 |
| 5,431,647 | 7/1995 | Purcell, Jr. et al. | 606/16 |
| 5,441,497 | 8/1995 | Narcisco, Jr. | 606/15 |

FOREIGN PATENT DOCUMENTS

| | | |
|---|---|---|
| 0 214 712 | 3/1987 | European Pat. Off. . |
| 0292621A1 | 11/1988 | European Pat. Off. ........ A61B 17/36 |
| 0 439 629 A1 | 8/1991 | European Pat. Off. . |
| WO94/17434 | 8/1994 | WIPO . |

OTHER PUBLICATIONS

U.S. application No. 08/303,605, Sinofsky, filed Sep. 9, 1994.

Primary Examiner—Michael Buiz
Assistant Examiner—Mark S. Leonardo
Attorney, Agent, or Firm—Thomas J. Engellenner; Lahive & Cockfield

[57] ABSTRACT

Phototherapeutic instruments are disclosed having integral stopper devices which limit the penetration of an optical fiber during tissue penetrating phototherapy. In one preferred embodiment, a fluted outer sheath is disposed about an internal optical fiber. The fluted sheath is configured to expand during penetration of the optical fiber into a patient's tissue. As the fluted elements expand, the present a much larger cross-sectional area which resists further penetration of the instrument beyond a predetermined desirable distance. The invention is useful in limiting an optically-transmissive fiber's penetration and, thereby, reduce the possibility of perforation of a body lumen or organ. The invention is particularly useful in placing a ablative laser radiation device into the ventricle of the heart when performing arrhythmia-correcting laser ablative procedures or when revascularizing the heart percutaneously. The stopper devices limit penetration and stabilize the optically-transmissive tip during such procedures.

12 Claims, 2 Drawing Sheets

PHOTOTHERAPY APPARATUS WITH INTEGRAL STOPPER DEVICE

BACKGROUND OF THE INVENTION

The technical field of this invention is phototherapy and, in particular, instruments employing optical fibers or other flexible light waveguides to deliver radiation to a targeted biological sight.

Fiber optic phototherapy is a increasing popular modality for the diagnosis and/or treatment of a wide variety of diseases. For example, in surgery, infrared laser radiation will often be delivered to a surgical site via a hand-held instrument incorporating an optically transmissive fiber in order to coagulate blood vessels or cauterize tissue. Similar fiber optic delivery systems have been proposed for endoscopic or catheter-based instruments to deliver therapeutic radiation to a body lumen or cavity. U.S. Pat. No. 4,336,809 (Clark) and U.S. Reissue Pat. No. RE 34,544 (Spears) disclose that hematoporphyrin dyes and the like selectively accumulate in tumorous tissue and such accumulations can be detected by a characteristic fluorescence under irradiation with blue light. These patents further teach that cancerous tissue that has taken up the dye can be preferentially destroyed by radiation (typically high intensity red light) that is absorbed by the dye molecules during phototherapy.

Others have proposed the use of fiber-delivered radiation to treat artherosclerotic disease. For example, U.S. Pat. No. 4,878,492 (Sinofsky et al.) discloses the used of infrared radiation to heat blood vessel walls during balloon angioplasty in order to fuse the endothelial lining of the blood vessel and seal the surface. Another application of fiber-delivered radiation is disclosed in U.S. Pat. No. 5,053,033 (Clarke) which teaches that restenosis following angioplasty can be inhibited by application of UV radiation to the angioplasty site to kill smooth muscle cells which would otherwise proliferate in response to angioplasty-induced injuries to blood vessel walls.

In yet another application, phototherapeutic instruments are employed to treat electrical arrhythmia of the heart. In such applications, a catheter having a fiber optic component is fed via a major artery into a patient's heart. Once inside the heart, a catheter senses electrical impulses with electrical contacts on its outer sheath or other catheter elements in order to locate the source of arrhythmia. Once located, the phototherapeutic component is activated to "ablate" a portion of the inner heart wall. By coagulating the tissue in the vicinity of the arrhythmia source, the likelihood that the parent's heart will continue to experience arrhythmia is thus reduced.

In other applications, laser radiation can be used in conjunction with a similar catheter instrument inside a patient's heart to increase blood flow to oxygen starved regions of the heart muscle. In such procedures, the laser radiation is used to form small holes into the heart muscle so that the oxygen-depleted tissue is bathed with blood from the ventricular cavity.

In all of these applications, there is the potential for damage to the patient's internal organs, especially the heart, if the light-emitting fiber is inserted too far into the patient's tissue. Particularly, in the case of the heart muscle, perforation of the heart wall can have very dangerous effects.

Accordingly, there exists a need for better apparatus for fiber-optic phototherapy. In particular, devices that can "stop" an optical fiber from perforating a patient's organs would meet a particularly important need in the field of minimally-invasive phototherapeutic surgery. Moreover, a device that can help stabilize the phototherapeutic instrument in operation (such as within the chambers of a rapidly beating heart) would also be particularly useful.

SUMMARY OF THE INVENTION

Phototherapeutic instruments are disclosed having integral stopper devices which limit the penetration of an optical fiber tip. In one preferred embodiment, a fluted outer sheath is disposed about an internal optical fiber. The fluted sheath is configured to fold into an expanded form during penetration into a patient's tissue. As the sheath is forced back and expands, the optically-transmissive assembly presents a much larger cross-sectional area which prevents penetration of the instrument beyond a pre-determined desirable distance.

The invention is particularly useful in limiting an optically-transmissive fiber's penetration and, thereby, reduce the possibility of perforation of a body lumen or organ. The invention is particularly useful in placing a ablative laser radiation device into the ventricle of the heart when performing arrhythmia-correcting laser ablative procedures or when revascularizing the heart percutaneously. In these types of procedures, the surgeon seeks to partially penetrate the heart muscle while not fully perforating the heart wall. The stopper devices of the present invention limit penetration and stabilized the optically-transmissive tip during phototherapy.

The invention will next be described in connection with certain preferred embodiments. However, it should be clear that various changes and modifications can be made by those skilled in the art without departing from the spirit or scope of the invention.

DETAILED DESCRIPTION

Figure 1:
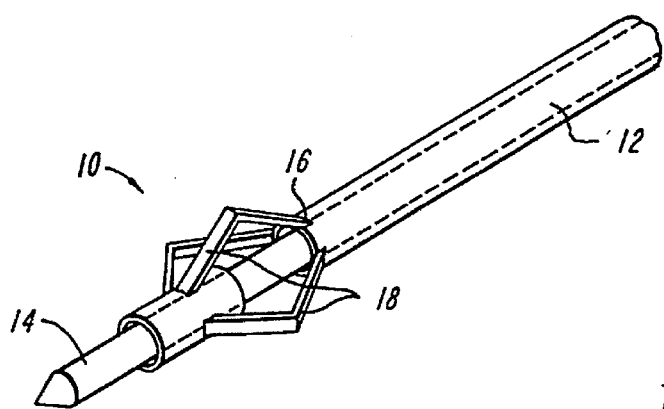
FIG. 1 a schematic, perspective field of the distal end of a phototherapeutic apparatus and integral stopper device in accordance with the present invention.

In FIG. 1 a phototherapeutic apparatus 10 is illustrated having a tubular sheath 12 and an inner optically-transmissive fiber element 14. The distal end of the sheath 12 is fluted such that axial compression of the sheath results in expansion of strut elements 18 in the fluted region 16.

Figure 2:
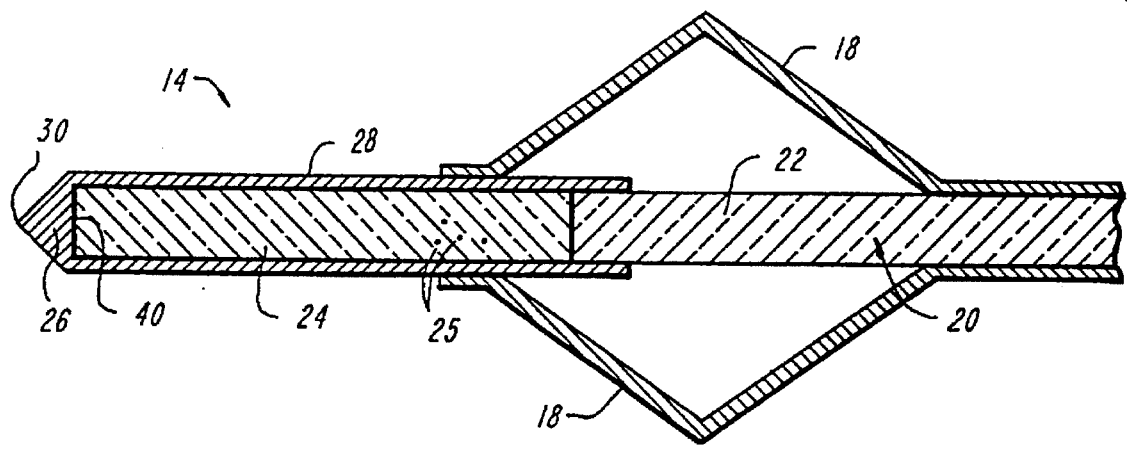
FIG. 2 is a cross-sectional illustration of the phototherapeutic apparatus of FIG. 1.

FIG. 2 is a more detailed cross-sectional view of the distal end of the apparatus of FIG. 1. The optically-transmissive element is shown having an optical fiber 20 with an optically transmissive core 22 surrounded by a cladding, and buffer coating. The end face of fiber core 22 is inserted into a housing 28 which contains a scattering medium 24 with optional individual scatterer particles 25. Preferably, the medium 24 has a greater refractive index than the housing 28. At the distal end of the housing 28, and end cap 26 can be disposed. Optionally, the end cap may also be fitted with a reflective mirror 40. The end cap can further be ground or polished to a point 30 to facilitate penetration of body tissue.

Light propagating through the optical fiber core 22 is transmitted into the scatterer medium and scattered in an cylindrical pattern along the length of the assembly 14. Each time the light encounters a scatterer particle, it is deflected and, at some point, the net deflection exceeds the critical angle for internal reflection at the interface between the housing 28 and the medium 24. When this happens the light will exit. The housing can either be made sufficiently long to ensure that virtually all of the light entering it is eventually scattered and diffused in a single path, or as noted above, a reflective mirror can be fitted to the distal end of each diffuser assembly. When a mirror is employed, light propagating through the medium 24 will be at least partially scattered before it reaches mirror 40. Light which does not exit during this initial pass through the tip will be reflected by mirror 40 and returned through the tip assembly. During the second pass, the remaining radiation (or at least a major portion of this returning radiation) again encounters the scatterers which provide further circumferential diffusion of the light.

An exemplary manufacturing process suitable for joining a diffuser assembly to a glass-clad or polymer-clad optical fiber having an outer diameter of about 50 to about 1000 micrometers can begin by stripping off the buffer from the end of the optical fiber, e.g., exposing about two or three millimeters of the inner fiber core and its cladding. (It is not necessary to strip the cladding away from the core.) Prior to stripping, the fiber end face preferably should be prepared and polished as known in the art to minimize boundary or interface losses. A transparent tubular structure which will form the housing for the scatterer medium is then slipped over the prepared fiber end and, preferably slid beyond the fiber end. For example, if a tip assembly of about 20 millimeters is desired, the tubing can be about 100 millimeters long and slid over about 75 millimeters of the fiber, leaving an empty lumen of about 25 millimeters in front of the fiber end face. In one preferred embodiment, the housing is Teflon® FEP tubing, available, for example, from Zeus Industries (Raritan, N.J.).

The assembly is then injected with a scatterer-loaded material, such as a silicone, epoxy or other polymeric material(if a solid diffuser is desired) or a suitable liquid, such as water or a deuterium oxide solution, containing colloidal scatterer particles, such as silica, alumina, or titania, (if a liquid diffuser is desired). One exemplary scatterer medium can be formulated by mixing 70 parts of clear silicone, Mastersil™ Formula 151-Clear (available from Masterbond, Inc. of Hackensack, N.J.) with one part of titania filled silicone, Mastersil™ Formula 151-White (also available from Masterbond), and a conventional silicone curing or hardening agent. The tube lumen should be completely filled with the silicone, epoxy or other carrier mixture to avoid entrapment of air bubbles. The reflector (e.g., an aluminum, gold or other reflector-coated plug) is inserted into the distal end of the tube. The reflector at the distal end of the scatterer tube can be a deposited metal or dielectric coating. In one preferred embodiment, a room temperature hardening agent is used and the diffuser assembly is simply allowed to solidify overnight.

It should be clear that the manufacturing processes described above are merely illustrative, and various alternative techniques can be practiced to construct the fiber tip assemblies of the present invention. For example, automated extrusion methods and/or injection molding approaches can be employed to mass produce fibers with integral diffusive tip assemblies.

Various other diffusive tip assemblies can be employed in the present invention. For a detailed discussion of various alternative embodiments see commonly-owned co-pending U.S. patent application Ser. No. 08/303,605 filed Sep. 9, 1994, entitled "PHOTOTHERAPY METHODS AND APPARATUS", by Edward L. Sinofsky, incorporated herein by reference.

Figure 3:
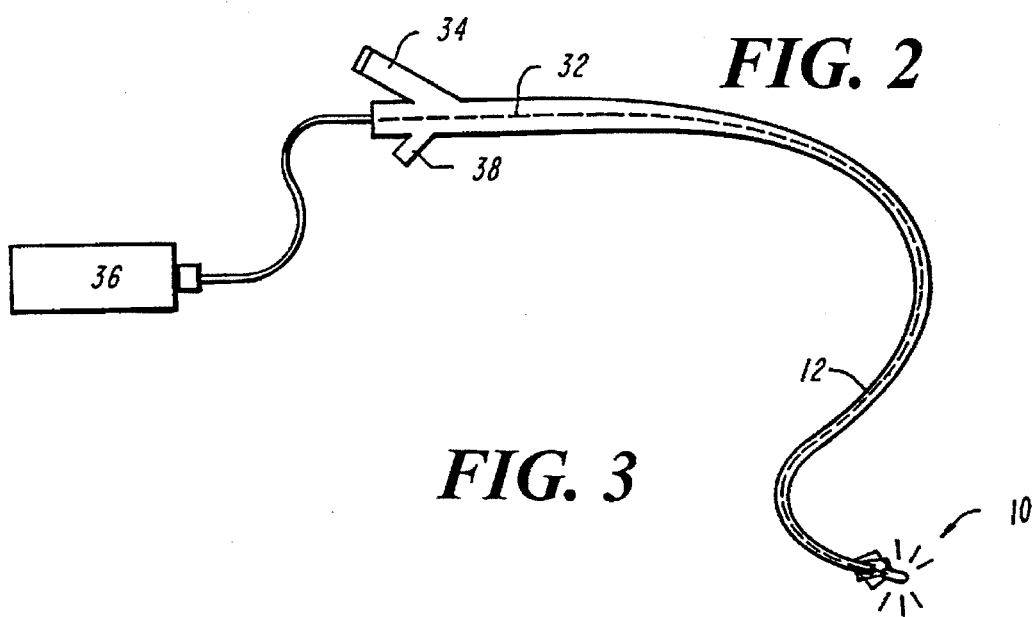
FIG. 3 is a schematic view of the present invention as part of a catheter or endoscopic system.

In FIG. 3, the phototherapeutic apparatus in the present invention 10 is shown schematically in operation. The diffuser apparatus with its fluted stopper is coupled to a source of phototherapeutic radiation 36, (e.g., a laser) and positioned within a patient's body to provide phototherapy. As shown in FIG. 3, the diffuser assembly can be designed to fit within a standard guiding catheter 32. The catheter 32 can further include electrical sensing elements 34 and/or at least one additional channel 38 for introduction of saline or therapeutic solutions.

Figure 4A:
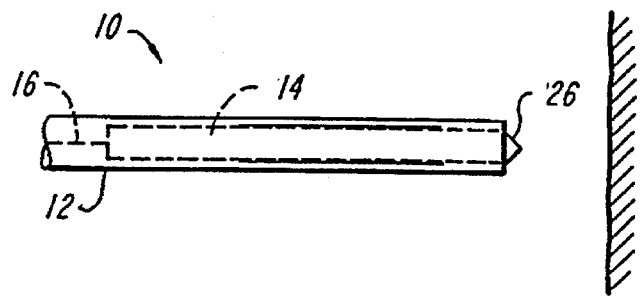
FIG. 4A illustrates the phototherapeutic apparatus of the present invention deployed in an initial position prior to contacting the surface of a body organ or lumen.

In FIG. 4A, the use of the phototherapeutic apparatus of the present invention is shown schematically. As illustrated, the instrument 10 is positioned next to a segment of a patient's body tissue where penetration and radiation is desired. As shown, the apparatus includes an outer sheath 12 having a fluted region 16 and an inner optically-transmissive fiber element 14 with tip 26. In one preferred embodiment, the fiber 14 and sheath 12 are constructed with sufficient clearance to permit saline or other therapeutic liquids to be released during the procedure. In particular, saline flushing of the fiber tip 14 may be desirable to cool the tissue surface proximal to the treatment site.

Figure 4B:
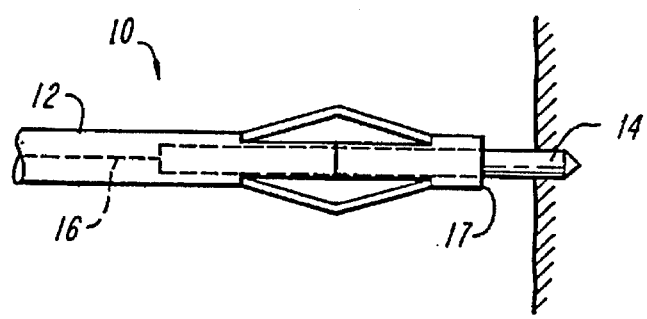
FIG. 4B is a further illustration of the apparatus of FIG. 4A after initial penetration of body tissues.

In FIG. 4B, initial penetration of the apparatus 10 is shown. In this illustration, the optically-transmissive fiber has penetrated the patient's tissue but the end 17 of sheath 22 has not yet touched the tissue surface.

Figure 4D:
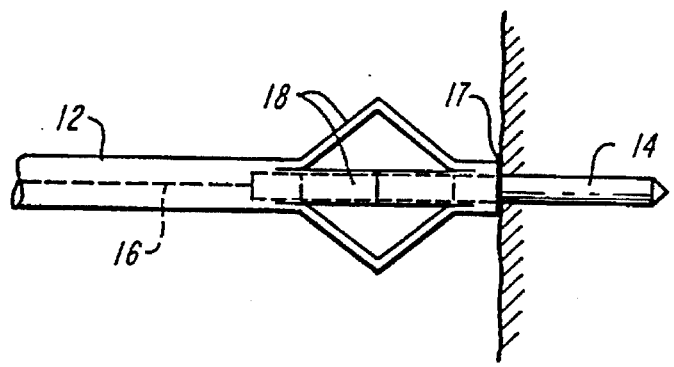
FIG. 4D is a further illustration of the apparatus of FIG. 4A in which the stopper device is fully deployed.
Figure 4C:
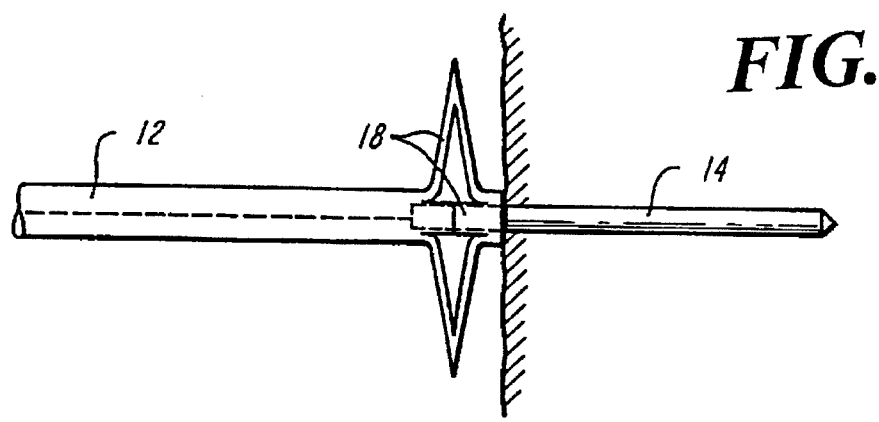
FIG. 4C is a further schematic illustration of the penetration of the phototherapeutic apparatus of FIG. 4A in which the stopper mechanism is partially deployed.

In FIG. 4C, the fiber 14 has penetrated further into the patient's tissue and the sheath 12 has now been pushed into a position abutting the patient's tissue. As the instrument is advanced, the fluted region 16 begins to expand due to the compressive forces exerted during penetration. Struts 18 are pushed out radially from the body of the apparatus.

In FIG. 4D, the apparatus is shown in a fully deployed position wherein a predetermined length of the optical fiber 14 has now penetrated the patient's body tissue and the radially-expanded struts 1 g have been fully compressed into a maximal position creating a large cross-sectional obstruction to further penetration.

Various materials can be used to form the outer sheath including, for example, Telfon® and other fluorocarbon polymers. The struts can be formed by axial slices at various locations on the sheath. For example to construct a four strut stopper device, one would make four longitudinal cuts into the sheath, separated by 90° from each other. The length of the cuts will determine the radial extent of the stopper. In one embodiment it may also be desirable to fill the sheath polymer with a radio-opaque substance, such as barium in order to permit visualization under angiography.

We claim:

1. A phototherapeutic apparatus comprising
    an optical fiber having a proximal end and a distal end, the proximal end adapted for coupling to a source of phototherapeutic radiation; and
    the distal end having means for directing such radiation into biological tissue;

the apparatus further comprising a sheath surrounding said optical fiber and having a fluted region which is capable of expanding upon penetration of the optical fiber into biological tissue.

2. The apparatus of claim 1 wherein the optical fiber has a pointed distal end.

3. The apparatus of claim 1 wherein the apparatus further comprises a light diffusing tip assembly connected to the distal end of said optical fiber to diffuse radiation into said tissue.

4. The apparatus of claim 3 wherein the diffusive tip further comprises a light transmissive housing adapted with the distal end of the fiber, the housing having a light scattering medium disposed therein.

5. The apparatus of claim 4 wherein the housing further includes an end cap having a reflective surface such that light radiation propagating through said fiber and enters the scattering medium and a portion of the radiation is emitted outward through said housing, and another portion is reflected by the reflective surface of the end cap for re-transmission through said scattering medium and further outward emission.

6. The apparatus of claim 4 wherein the scattering medium further comprises a medium having light-scattering particles dispersed therein.

7. The apparatus of claim 6 wherein the scatterer particles are chosen from the group consisting of alma, silica, titania compound and mixtures thereof.

8. The apparatus of claim 3 wherein the tip element is a pointed element.

9. The apparatus of claim 1 wherein the fluted region is made of a radio-opaque material.

10. The apparatus of claim 4 wherein the housing is made of a polymeric material.

11. The apparatus of claim 10 wherein the polymeric material of the housing is a fluorocarbon polymer.

12. The apparatus of claim 1 wherein the optical fiber and surrounding sheath are constructed with sufficient clearance therebetween for delivery of therapeutic liquids to the radiation site.

* * * * *